(12) United States Patent
Zang et al.

(10) Patent No.: US 9,786,848 B2
(45) Date of Patent: Oct. 10, 2017

(54) NANOFIBER-BASED HETEROJUNCTION APPROACH FOR HIGH PHOTOCONDUCTIVITY ON ORGANIC MATERIALS

(75) Inventors: Ling Zang, Salt Lake City, UT (US); Yanke Che, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 987 days.

(21) Appl. No.: 13/879,574

(22) PCT Filed: Oct. 14, 2011

(86) PCT No.: PCT/US2011/056394
§ 371 (c)(1),
(2), (4) Date: Sep. 30, 2013

(87) PCT Pub. No.: WO2012/051553
PCT Pub. Date: Apr. 19, 2012

(65) Prior Publication Data
US 2014/0147670 A1     May 29, 2014

Related U.S. Application Data

(60) Provisional application No. 61/393,280, filed on Oct. 14, 2010.

(51) Int. Cl.
*H01L 51/00* (2006.01)
*C07D 471/06* (2006.01)
*H01L 51/42* (2006.01)

(52) U.S. Cl.
CPC ........ *H01L 51/0072* (2013.01); *C07D 471/06* (2013.01); *H01L 51/4246* (2013.01);
(Continued)

(58) Field of Classification Search
USPC ............................................. 428/378; 427/74
See application file for complete search history.

(56) References Cited

U.S. PATENT DOCUMENTS

| | | |
|---|---|---|
| 5,986,206 A | 11/1999 | Kambe et al. |
| 6,203,864 B1 | 3/2001 | Zhang et al. |
| (Continued) | | |

FOREIGN PATENT DOCUMENTS

| | | |
|---|---|---|
| AU | 2003204543 | 3/2005 |
| CN | 1974486 | 6/2007 |
| (Continued) | | |

OTHER PUBLICATIONS

Charvet et al., "Block-Copolymer-Nanowires with Nanosized Domain Segregation and High Charge Mobilities as Stacked p/n Heterojunction Arrays for Repeatable Photocurrent Switching"; J. Am. Chem. Soc. 2009, V 131, p. 18030-18031.

(Continued)

*Primary Examiner* — Lynda Salvatore
(74) *Attorney, Agent, or Firm* — Thorpe North & Western, LLP

(57) ABSTRACT

The present disclosure provides methods and compositions for an organic nanofiber-based heterojunction material, comprising nano fibers of an acceptor molecule, the nano fibers coated with a donor molecule, where the acceptor molecule contains a group and the donor molecule contains a companion group, wherein the group and companion group enables strong binding between the acceptor molecule and donor molecule, the strong binding providing for efficient forward electron transfer between the acceptor molecule and donor molecule, and wherein the group and companion group minimize charge carrier recombination between the acceptor molecule and the donor molecule.

16 Claims, 7 Drawing Sheets

(52) U.S. Cl.
CPC ......... *H01L 51/0053* (2013.01); *Y02E 10/549* (2013.01); *Y02P 70/521* (2015.11); *Y10T 428/2938* (2015.01)

(56) References Cited

U.S. PATENT DOCUMENTS

| | | | |
|---|---|---|---|
| 6,882,767 | B2 | 4/2005 | Yang et al. |
| 7,239,769 | B2 | 7/2007 | Yang et al. |
| 7,442,320 | B2 | 10/2008 | Lee |
| 7,482,621 | B2 | 1/2009 | Yang et al. |
| 7,554,111 | B2 | 6/2009 | Yang et al. |
| 7,645,933 | B2 | 1/2010 | Narkis et al. |
| 7,720,326 | B2 | 5/2010 | Wu et al. |
| 7,736,741 | B2 | 6/2010 | Maruyama et al. |
| 7,750,285 | B2 | 7/2010 | Nagamune et al. |
| 8,003,979 | B2 | 8/2011 | Cho et al. |
| 8,212,235 | B2 | 7/2012 | Wang et al. |
| 8,440,997 | B2 | 5/2013 | Wang et al. |
| 2001/0001681 | A1 | 5/2001 | Zhang et al. |
| 2003/0008172 | A1 | 1/2003 | Leclerc et al. |
| 2004/0124755 | A1 | 7/2004 | Zhang et al. |
| 2005/0045867 | A1 | 3/2005 | Ozkan et al. |
| 2006/0272701 | A1 | 12/2006 | Ajayan et al. |
| 2007/0128101 | A1 | 6/2007 | Zhang et al. |
| 2007/0176163 | A1 | 8/2007 | Drolet et al. |
| 2008/0102017 | A1 | 5/2008 | Maruyama et al. |
| 2008/0310790 | A1 | 12/2008 | Wu et al. |
| 2009/0108255 | A1 | 4/2009 | Bazan |
| 2009/0120491 | A1 | 5/2009 | Berson et al. |
| 2009/0179192 | A1 | 7/2009 | Kamins |
| 2009/0205713 | A1 | 8/2009 | Mitra et al. |
| 2009/0233374 | A1 | 9/2009 | Zang et al. |
| 2009/0235988 | A1 | 9/2009 | Jenekhe et al. |
| 2009/0314350 | A1 | 12/2009 | Jung et al. |
| 2010/0025662 | A1 | 2/2010 | Cho et al. |
| 2010/0143679 | A1 | 6/2010 | Stupp et al. |
| 2010/0147674 | A1 | 6/2010 | Krivoshlykov |
| 2010/0197039 | A1 | 8/2010 | Zang et al. |
| 2010/0206362 | A1 | 8/2010 | Flood |
| 2010/0288343 | A1* | 11/2010 | Sotzing ............... B82Y 10/00 136/252 |
| 2011/0220191 | A1 | 9/2011 | Flood |
| 2011/0220194 | A1 | 9/2011 | Kurtin et al. |

FOREIGN PATENT DOCUMENTS

| | | |
|---|---|---|
| FR | 2849539 | 7/2004 |
| JP | 2904346 | 6/1999 |
| JP | 2010053109 | 3/2010 |
| KR | 20060083037 | 7/2006 |
| KR | 20080018559 | 2/2008 |

OTHER PUBLICATIONS

Che et al., "Ultrathin n-Type Organic Nanoribbons with High Photoconductivity and Application in Optoelectronic Vapor Sensing of Explosives"; J. AM. Chem. Soc. 2010, V 132, p. 5743-5750.

Herrikhuyzen et al., "Synthesis of n-Type Perylene Bisimide Derivatives and Their Orthogonal Self-Assembly with p-Type Oligo(p-phenylene vinylene)s"; J. AM. Chem. Soc. 2004, V 126, p. 10021-10027.

Hizume et al., "Chiroselective Assembly of a Chiral Porphyrin-Fullerene Dyad: Photoconductive Nanofiber with a Top-Class Ambipolar Charge-Carrier Mobility"; J.AM. Chem. Soc. 2010, V 132, p. 6628-6629.

Li W, et al.; "Use of side-chain incompatibility for tailoring long-range p/n heterojunctions: photoconductive nanofibers formed by self-assembly of an amphiphilic donor-acceptor dyad consisting of oligothio phene and perylenediimide"; Jul. 5, 2010; 5(7): 1566-72; vol. 10.1002/asia.201000111.

Mo et al., "Fabrication and Photoconductivity Study of Copper Phthalocyanine/Perylene Composite with Bulk Heterojunctions Obtained by Solution Blending"; J. Phys. Chem. B 2005, V 109, p. 7659-7663.

Wicklein et al., "Self-Assembly of Semiconductor Organogelator Nanowires for Photoinduced Charge Separation" vol. 3, No. 5, p. 1107-1114, 2009 Acs Nano.

Zhao, et al.; "Layer-by-Layer Deposited Multilayer Films of Oligo(pyrenebutyric acid) and a Perylene Diimide Derivative: Structure and Photovoltaic Properties"; Langmuir 2008, vol. 24, 4380-4387; final form Jan. 25, 2008.

* cited by examiner

US 9,786,848 B2

NANOFIBER-BASED HETEROJUNCTION APPROACH FOR HIGH PHOTOCONDUCTIVITY ON ORGANIC MATERIALS

GOVERNMENT INTEREST

This invention was made with government support under Grant No. CAREER CHE 0641353, CBET 730667 awarded by the National Science Foundation (NSF) and under Grant No. 2009-ST-108-LR0005 awarded by the Department of Homeland Security (DHS). The government has certain rights to this invention.

FIELD OF THE INVENTION

The present invention relates generally to photoconductive organic semiconductor materials. More particularly, the present invention relates to compositions and methods of making photoconductive organic semiconductor materials. As such, the present invention relates to the fields of chemistry and material science.

BACKGROUND OF THE INVENTION

Photoconductive organic materials have attracted increasing interest due to their potential applications in photodetectors, sensors, and photovoltaics. However, the available organic materials are very limited due to their intrinsic low charge carrier density and mobility. Although bulk heterojunctions of electron donors (D) and acceptors (A) can allow for generation of photocurrent, the formation of charge-transfer complexes and the lack of long-range charge transport pathways can result in the loss of photogenerated charge carriers through recombination. One-dimensional organic nanostructures assembled via π-π interactions present promising candidates for highly photoconductive materials due to their enhanced charge carrier mobility. However, only a few examples of photoconductive one-dimensional nanostructures have been reported, and most are focused on covalently linked D-A molecules. Disadvantages of these systems include complicated molecular design and synthesis, and challenges in optimizing the intermolecular assembly to avoid charge carrier recombination, making them impractical in large-scale applications. As such, research and developmental efforts continue in the field of photoconductive organic materials.

SUMMARY OF THE INVENTION

It has been recognized that it would be advantageous to provide organic semiconductor materials having a simple nanofiber-based heterojunction to achieve high photoconductivity and fast photoresponse.

The present disclosure provides organic semiconductor heterojunction materials comprising nanofibers of an acceptor molecule, the nanofibers coated with a donor molecule; wherein the acceptor molecule contains a group and the donor molecule contains a companion group, where the group and companion group can enable strong binding between the acceptor molecule and donor molecule, the strong binding providing for efficient forward electron transfer between the acceptor molecule and donor molecule, and where the group and companion group can minimize charge carrier recombination between the acceptor molecule and the donor molecule.

Additionally, a method of manufacturing nanofiber-based heterojunction materials can comprise dissolving an acceptor molecule in an organic solution, the acceptor molecule containing a group; mixing the organic solution with an second organic solution to form a nanofiber; and drop-casting a donor molecule dissolved in a third organic solution onto the nanofibers thereby forming coated nanofibers, the donor molecule having a companion group. As discussed above, the group and companion group can enable strong binding between the acceptor molecule and donor molecule, the strong binding providing for efficient forward electron transfer between the acceptor molecule and donor molecule, and the group and companion group can minimize charge carrier recombination between the acceptor molecule and the donor molecule.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

The present invention will become more fully apparent from the following description and appended claims, taken in conjunction with the accompanying drawings. It is to be understood that these drawings merely depict exemplary embodiments of the present invention and they are, therefore, not to be considered limiting of its scope. It will be readily appreciated that the components of the present invention, as generally described and illustrated in the figures herein, could be arranged, sized, and designed in a wide variety of different configurations. Nonetheless, the invention will be described and explained with additional specificity and detail through the use of the accompanying drawings in which:

Figure 4:
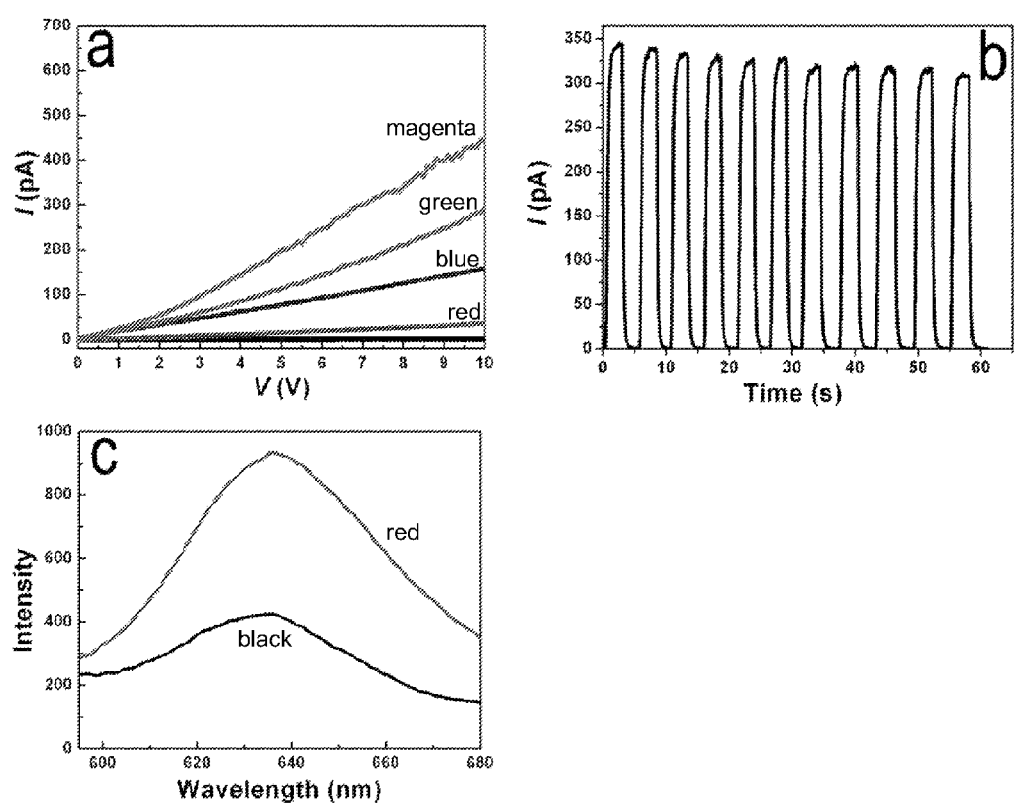
FIG. 4 provides various plots showing optical and electrical characterization of the nanofibril heterojunctions: a) I-V curves measured over the A-1 nanofibers with increasing deposition of D-1 through drop-casting of the ethanol solution (0.1 mM) (in order of ascension black: pristine nanofibers containing 7.5 nmol A-1; red, blue, green, magenta: deposition of 1, 2, 3, 4 nmol D-1, respectively); white light irradiation was set at a power density of 0.17 mW/mm$^2$, b) Photocurrent measured at 10 V of bias in response to turning on and off the white light irradiation (0.17 mW/mm$^2$), c) Fluorescence spectra of A-1 nanofibers (containing 7.5 nmol A-1) measured before (red) and after (black) deposition of 1 nmol D-1 (Electrode-pairs used: 5 µm in gap, 14 µm in width with all measurements were carried out under ambient conditions)
Figure 5:
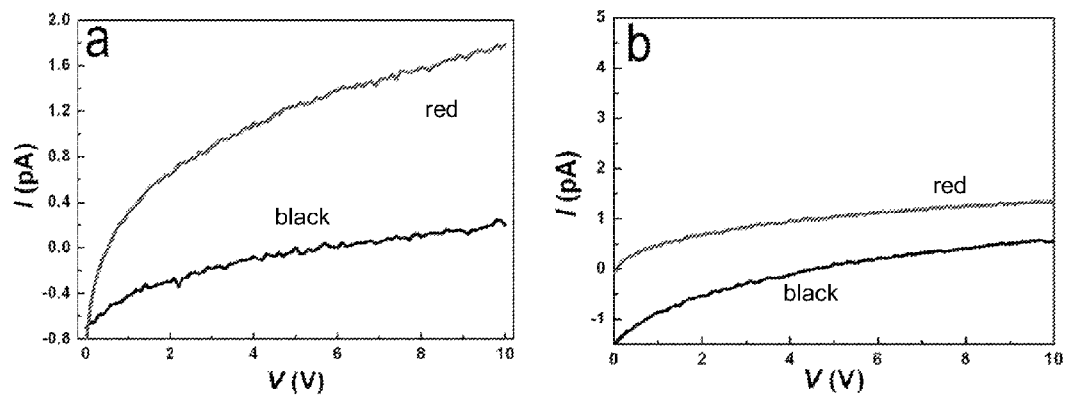
Figure 6:
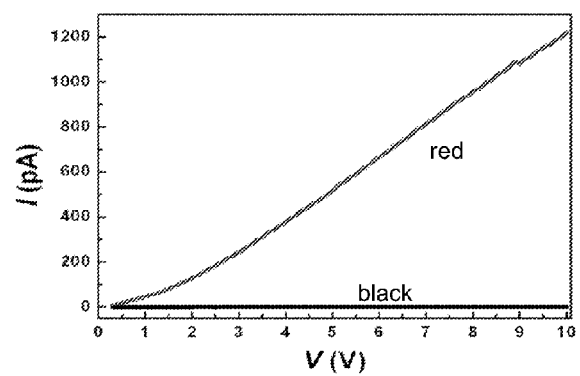
Figure 7:
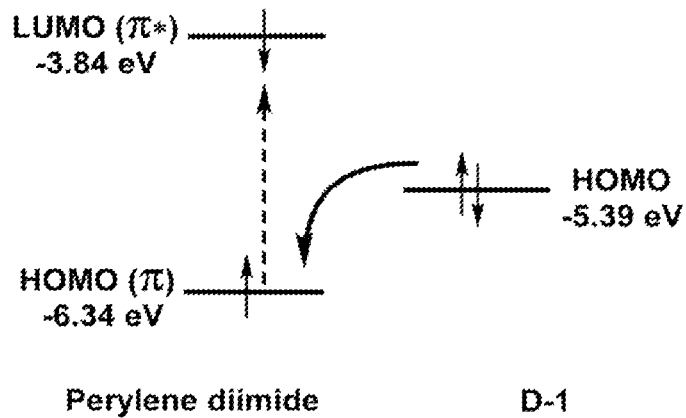
Figure 8:
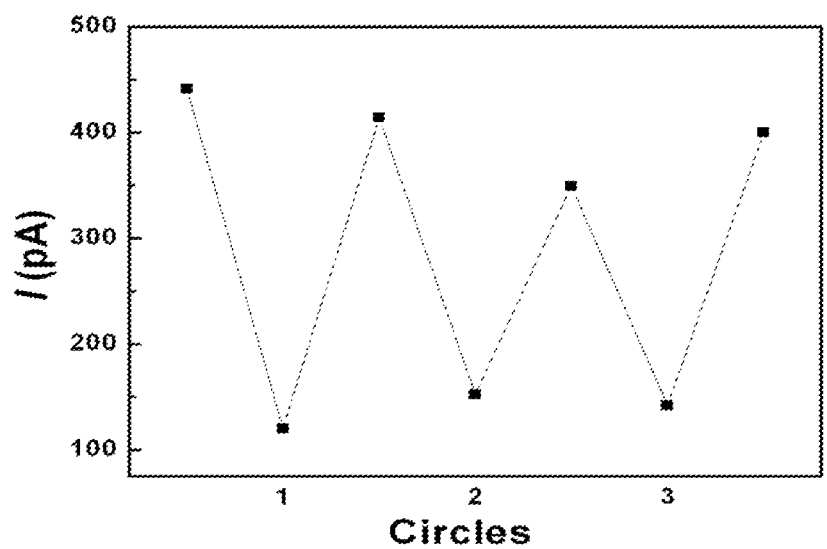
Figure 9:
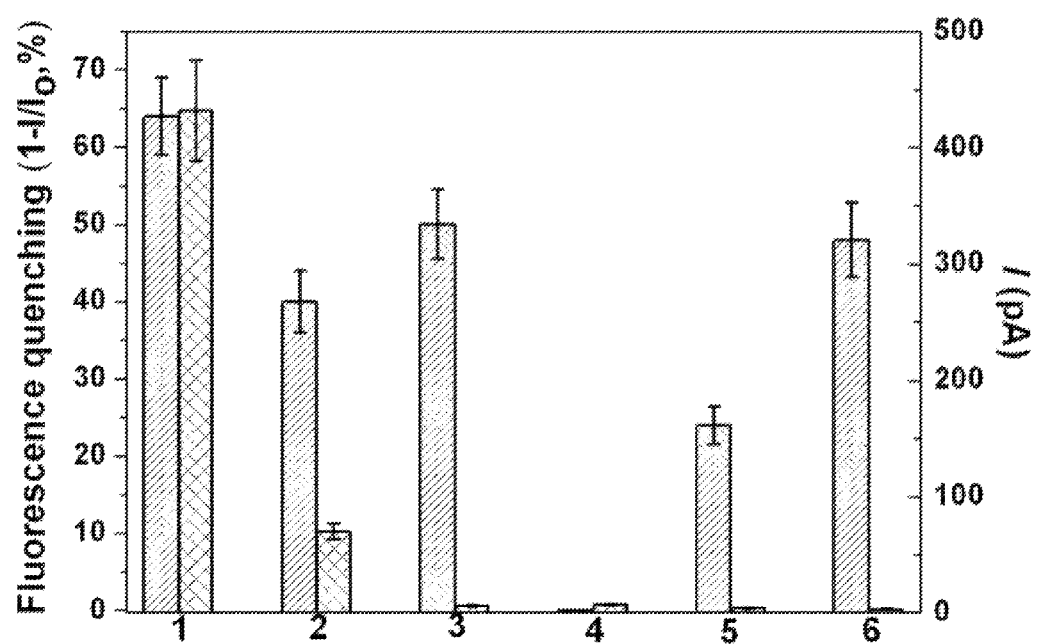

FIG. 5 is a) I-V curve measured over pristine A-1 nanofibers in the dark (black) and under white light irradiation of power density 0.17 mW/mm$^2$ (red); and b) I-V curve measured over D-1 film in the dark (black) and under white light irradiation of power density 0.17 mW/mm$^2$ (red);

FIG. 6 shows I-V curves measured over the nanofibers of A-1 (7.5 nmol) coated with 4 nmol D-1 molecules as deposited on a wide electrode-pair (90 µm in width and 5 µm in gap): (black) in the dark and (red) under white light irradiation of power density 0.17 mW/mm$^2$;

FIG. 7 shows energy level of HOMO ($\pi$) and LUMO ($\pi^*$) orbitals of perylene diimide (A) and HOMO orbital of D-1 (−5.39 eV) showing the favorable photoinduced electron transfer with large driving force (0.95 eV);

FIG. 8 shows I (pA) measurements of reversible photocurrent generation of A-1 nanofibers upon desorption and re-adsorption (circle) of D-1 molecules; and FIG. 9 is a bar graph comparing optical and electrical performance between various D/A heterojunctions (the dense line and sparse square columns denote fluorescence quenching and photocurrent measurement, respectively) 1. nanofibers of A-1 (7.5 nmol) deposited with 4 nmol D-1; 2. nanofibers of A-1 (7.5 nmol) deposited with 60 nmol D-2; 3. nanofibers of A-1 (7.5 nmol) deposited with 20 nmol D-3; 4. nanofibers of A-2 (7.5 nmol) deposited with 15 nmol D-1; 5. film of A-3 (10 nmol) deposited with 20 nmol D-1; 6. film of A-3 (10 nmol) deposited with 60 nmol D-3 (10 nmol and 60 nmol, respectively (electrode configuration and measurement conditions are the same as employed in FIG. 4).

DETAILED DESCRIPTION

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

It is noted that, as used in this specification and the appended claims, the singular forms "a," "an," and "the" include plural referents unless the context clearly dictates otherwise. Thus, for example, reference to "a lithium-magnesium compound" includes one or more of such materials, reference to "an additive" includes reference to one or more of such additives, and reference to "a heating step" includes reference to one or more of such steps.

Definitions

In describing and claiming the present invention, the following terminology will be used in accordance with the definitions set forth below.

As used herein, "heteroatom" refers to nitrogen, oxygen, phosphorus or sulfur. The terms "halo" and "halogen" refer to a fluoro, chloro, bromo, or iodo substituent. The term "cyclic" refers to having an alicyclic or aromatic ring structure, which may or may not be substituted, and may or may not include one or more heteroatoms.

As used herein, "alkyl" refers to a branched, unbranched, or cyclic saturated hydrocarbon group, which typically, although not necessarily, contains from 1 to about 50 carbon atoms, or 1 to about 40 carbon atoms, or 1 to about 30 carbon atoms for example. Alkyls include, but are not limited to, methyl, ethyl, n-propyl, isopropyl, n-butyl, isobutyl, t-butyl, octyl, and decyl, for example, as well as cycloalkyl groups such as cyclopentyl, and cyclohexyl, for example. The term "lower alkyl" refers to an alkyl group having from 1 to 6 carbon atoms. The term "higher alkyl" refers to an alkyl group having more than 6 carbon atoms, for example, 7 to about 50 carbon atoms, or 7 to about 40 carbon atoms, or 7 to about 30 carbon atoms or more. As used herein, "substituted alkyl" refers to an alkyl substituted with one or more substituent groups. The term "heteroalkyl" refers to an alkyl in which at least one carbon atom is replaced with a heteroatom. The term "functionalized alkyl" refers to an alkyl in which at least one carbon atom is replaced with an organic functional group. The organic functional group can be along the backbone of the alkyl or as a pendent. If not otherwise indicated, the term "alkyl" includes unsubstituted alkyl, substituted alkyl, functionalized alkyl, heteroalkyl, linear alkyl, and branched alkyl As used herein, "organic functional group" includes without limitation heteroatoms, aryls, alkenes, alkynes, alcohols, ketones, aldehydes, ethers, esters, carboxylic acids, amides, acyl halides, peroxides, carbonates, carboxylates, etc.

As used herein, "aryl" refers to a group containing a single aromatic ring or multiple aromatic rings that are fused together, directly linked, or indirectly linked (such that the different aromatic rings are bound to a common group such as a methylene or ethylene moiety). Aryl groups described herein may contain, but are not limited to, from 5 to about 50 carbon atoms, or 5 to about 40 carbon atoms, or 5 to 30 carbon atoms or more. Aryl groups include, for example, phenyl, naphthyl, anthryl, phenanthryl, biphenyl, diphenylether, diphenylamine, and benzophenone. The term "substituted aryl" refers to an aryl group comprising one or more substituent groups. The term "heteroaryl" refers to an aryl group in which at least one carbon atom is replaced with a heteroatom. If not otherwise indicated, the term "aryl" includes unsubstituted aryl, substituted aryl, and heteroaryl.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Invention

The present inventors have discovered a simple nanofiber-based heterojunction approach to achieve high photoconductivity and fast photoresponse. Such materials can have a large on/off ratio above $10^4$ for organic semiconductor materials. Such materials generally provide adsorption of donor (D) molecules onto acceptor (A) nanofibers via hydrophobic interaction between alkyl side-chains. This approach opens a general way for developing photoconductive organic materials for optoelectronic devices.

As such, organic semiconductor heterojunction materials can comprise nanofibers of an acceptor molecule, the nanofibers coated with a donor molecule; where the acceptor molecule contains a group and the donor molecule contains a companion group such that the group and companion group can enable strong binding between the acceptor molecule and donor molecule, the strong binding providing for efficient forward electron transfer between the acceptor molecule and donor molecule. Further, the group and companion group can minimize charge carrier recombination between the acceptor molecule and the donor molecule.

In one embodiment, the donor molecule can be a carbazole. In one aspect, the core donor molecule can be a linear polycarbazole as either an oligomer or a polymer. Non-limiting examples of carbazoles can include selected from the group consisting of:

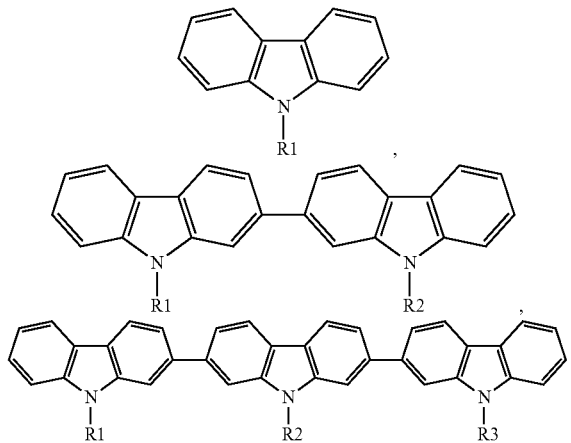

where R1, R2, and R3 are companion groups and are independently selected from the group consisting of H, branched alkyl, linear alkyl, substituted alkyl, unsubstituted alkyl, functionalized alkyls, and combinations thereof. In one aspect, R1, R2, and R3 can be independently selected from the group consisting of $C_2$-$C_{16}$ alkyls, $C_2$-$C_{16}$ alkyl ethers, $C_3$-$C_{20}$ branched alkyls. In another aspect, R1, R2, and R3 can be independently $C_2$-$C_{16}$ alkyls. In still another aspect, the donor molecule can be

The R1, R2, and R3 groups can be the same of different. In one aspect, at least one of R1, R2, and R3 can be different. In another aspect, R1, R2, and R3 can be the same.

In one embodiment, the acceptor molecule can be

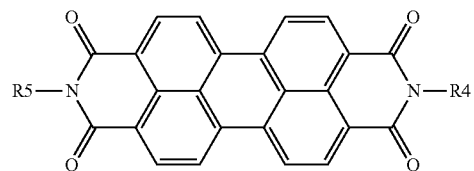

where R4 and R5 are groups and are independently selected from the group consisting of H, branched alkyl, linear alkyl, substituted alkyl, unsubstituted alkyl, functionalized alkyl, and combinations thereof. In one aspect, R4 and R5 can be independently selected from the group consisting of $C_2$-$C_{16}$ alkyls, $C_2$-$C_{16}$ alkyl ethers, $C_3$-$C_{20}$ branched alkyls. In another aspect, R4 and R5 can be independently $C_2$-$C_{16}$ alkyls.

As discussed herein, generally, R1 through R3 are the companion groups of the donor molecule which, when paired with R4 and R5 groups of the acceptor molecule, enable the strong binding for efficient forward electron transfer and minimize generated charge carrier recombination. Typically, both types of groups can be chosen to allow an interdigitated orientation of groups when donor molecules are coated on the acceptor molecules. In this configuration, the donor companion groups and the acceptor groups are present at an interface between the donor and acceptor molecules. In one embodiment, the acceptor groups and donor companion groups can be the same. In another embodiment, the acceptor groups and donor companion groups can be different. In one aspect, the acceptor groups and donor companion groups can be linear $C_2$-$C_{16}$ alkyl chains. In another aspect, the acceptor groups and donor companion groups can independently be linear $C_2$-$C_{16}$ alkyl chains such that the acceptor group is within 8 carbons in length of the donor companion group.

When discussing strong binding and efficient forward electron transfer, such characteristics of the present materials can be measured as function of photocurrent generation quantum efficiency. In one embodiment, the nanofiber-based heterojunction materials can have a photocurrent generation quantum efficiency of at least 8%. Additionally, the present materials can be beneficial for use in optoelectronic devices as they can have superior optoelectronic properties. In one aspect, the photocurrent response of the nanofiber-based heterojunction materials can have a response time of 200 ms.

In another aspect, the nanofiber-based heterojunction materials can have a fluorescence quenching of 30-90%. Further, the present materials can minimize generated charge carrier recombination.

Generally, the materials discussed herein can be of sufficient size and proportions such that the previously discussed functionality is met and therefore are not limited to any specific size or ratios. However, in one aspect, the nanofibers can be 1 μm to 10 μm in length. In another aspect, the nanofibers can be 10 nm to 100 nm wide. Further, in one embodiment, the nanofiber-based heterojunction materials have a molar ratio of donor molecule to acceptor molecule of 1:20 to 20:1, and in some cases 5:1.

A method of manufacturing nanofiber-based heterojunction materials can comprise dissolving an acceptor molecule in an organic solution, the acceptor molecule containing a group; mixing the organic solution with an second organic solution to form a nanofiber; and drop-casting a donor molecule dissolved in a third organic solution onto the nanofibers thereby forming coated nanofibers, the donor molecule having a companion group. As discussed above, the group and companion group can enable strong binding between the acceptor molecule and donor molecule, the strong binding providing for efficient forward electron transfer between the acceptor molecule and donor molecule, and the group and companion group can minimize charge carrier recombination between the acceptor molecule and the donor molecule.

Generally, the organic solutions can be chosen based on the desired solubility for the specific donor and acceptor molecules used in the materials synthesis. In one aspect, the organic solution can be chloroform. In another aspect, the second organic solution and/or the third organic solution can be an alcohol.

Generally, the acceptor molecules can be formed by functionalizing a corresponding core molecule through a proper choice of side groups, e.g., such as alkyl. The functionalization can be accomplished using chemical synthesis. Although other molecules such as 4,5,7-trinitrofluorenone-2-carboxylic acid may be suitable, the donor core can often be a perylene core. In one aspect, the core acceptor molecule is a perylene core.

The donor molecules can be also formed by functionalizing a corresponding donor core through proper side group attachment. Although a monocarbazole can be used, carbazole oligomers can also be suitable (i.e. 2-5 linearly linked carbazole groups).

Additionally, in one embodiment, the method can further comprise removing the donor molecule by washing the coated nanofibers with an organic solvent. This may be desirable when material performance degrades. These materials allow for relatively simple recycling or refreshing of the material by stripping the donor coating and recoating. Thus, the method can optionally further comprise reapplying a new donor molecule by drop-casting the new donor molecule dissolved in a fourth organic solution onto the nanofibers thereby forming new coated nanofibers, where the new donor molecule is selected from the group consisting of

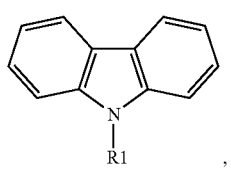

,

-continued

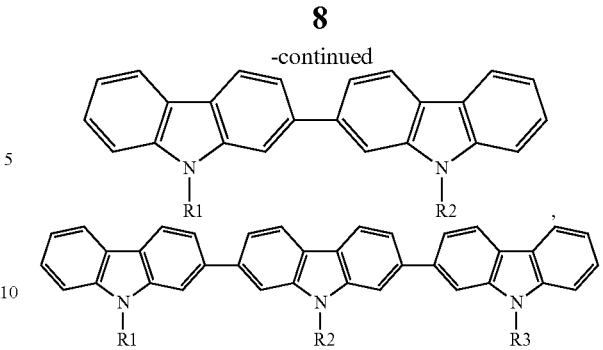

where R1, R2, and R3 are groups and are independently selected from the group consisting of: H, branched alkyl, linear alkyl, substituted alkyl, unsubstituted alkyl, functionalized alkyl, and combinations thereof.

EXAMPLES

Example 1

Synthesis of A-1, A-2, and A-3

Molecules A-1, A-2, A-3 were synthesized following the previously developed methods as described in *Acc. Chem. Res.* 41, 2008, 1596-1608, which is incorporated here by reference.

Example 2

Synthesis of D-1 and D-2

D-1 and D-2 were synthesized as follows:

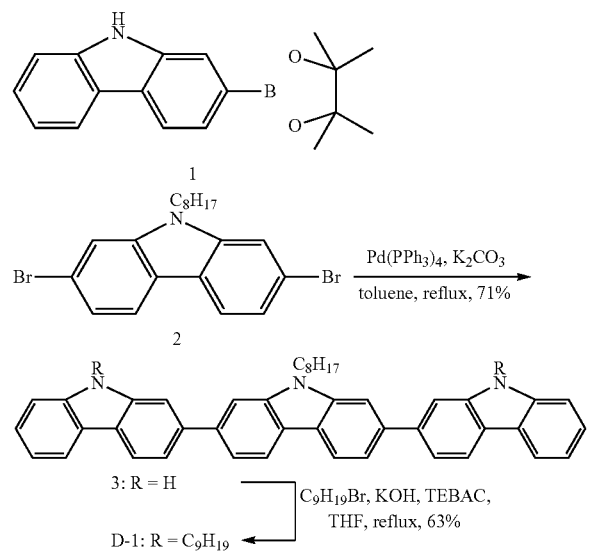

2,7-dibromo-9-octyl-9H-carbazole 2 (220 mg, 0.5 mmol), 9H-carbazole-2-boronic acid pinacol ester 1 (880 mg, 1.5 mmol) and benzyltriethylammonium chloride (50 mg) were added into a mixture of toluene (20 mL) and aqueous $K_2CO_3$ (2M, 8 mL), followed by three freeze-pump-thaw cycles of degassing. $Pd(PPh_3)_4$ (5 mg) was then added under argon protection, again followed by three freeze-pump-thaw cycles of degassing. The mixture was refluxed for 24 h and the organic phase was separated and evaporated. The product was purified by column chromatography on silica gel (hexane/THF, 4:2) and dried in vacuum. A 220 mg (71%) yield of compound 3 was obtained as a light brown powder. $^1$H NMR (THF-d8, 500 MHz): δ=10.33 (s, 2H), 8.15 (m, 4H), 8.07 (d, J=7.9, 2H), 7.82 (m, 4H), 7.6 (m, 4H), 7.43 (d, J=8.0, 2H), 7.34 (m, 2H), 7.15 (m, 2H), 4.56 (t, J=7.19, 2H), 1.99 (m, 2H), 1.29 (m, 10H), 0.83 (t, J=6.9, 3H). MALDI-TOF MS: m/z 609.33 (100%).

D-1: Compound 3 (0.01 mmol) was dissolved in 15 ml of THF, followed by addition of the phase transfer catalyst benzyltriethylammonium chloride (50 mg), $C_9H_{19}Br$ (0.1 ml) and KOH (6 mg, 0.1 mmol). The mixture was then stirred and refluxed for 2 h. The reaction mixture was poured into water and extracted by chloroform. The organic phase was collected, washed with brine, water and dried. The raw product thus obtained was further purified by column chromatography on silica gel (hexane/$CH_2Cl_2$, 100:1) and dried in vacuum. A 5.4 mg (63%) yield of compound D-1 was obtained as white powder. $^1$HNMR ($CDCl_3$, 500 MHz): δ=8.17 (m, 4H), 8.12 (d, J=7.5, 2H), 7.71 (m, 4H), 7.61 (m, 4H), 7.43 (d, J=8.0, 2H), 7.42 (m, 2H), 7.24 (m, 2H), 4.11 (t, J=6.9, 6H), 1.65 (m, 6H), 1.26-1.41 (m, 34H), 0.87 (t, J=6.9, 9H). MALDI-TOF MS: m/z 861.60 (100%).

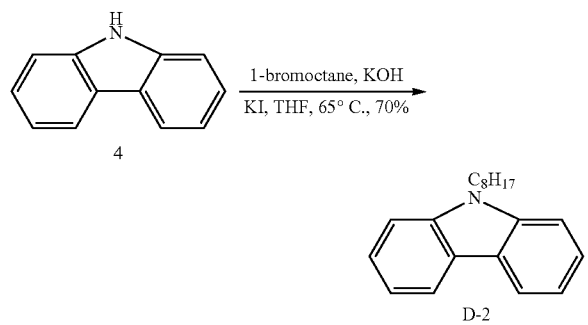

D-2: A mixture of 9H-Carbazole 4 (1.67 g, 10 mmol), KOH (0.84 g, 15 mmol), 1-Bromooctane (2.88 g, 15 mmol) and a small amount of KI (5%) in dry THF (100 mL) was stirred at 65° C. under argon atmosphere for 24 h. After cooling to room temperature, the reaction mixture was poured into water and the product was extracted with chloroform. The solvent was evaporated under reduced pressure, and the crude product was purified by column chromatography on silica gel (hexane as the fluent) to give a yellow oil product N-Octylcarbazole D-2 (1.95 g, 70%). $^1$H NMR (CDCl3, 500 MHz): δ ppm=8.09 (dd, J=8.0 Hz, 2H), 7.44 (ddd, J=6.5, 6.2 Hz, 2H), 7.39 (dd, J=8.0 Hz, 2H), 7.22 (ddd, J=7.0 Hz, 2H), 4.28 (t, J=7.5 Hz, 2H), 1.86 (tt, J=7.5 Hz, 2H), 1.24-1.40 (m, 10H), 0.86 (t, J=7.0 Hz, 3H).

Example 3

Fabrication of a Nanofibers and the Nanofibril Heterojunctions with D Molecules

A-1, A-2, and A-3 molecules were obtained according to Example 1. The A-1 nanofibers were fabricated by injecting 0.5 mL chloroform solution of A-1 molecules (0.15 mM) into 3 mL ethanol in a test tube followed by 5 hours of aging. The nanofibers formed can be transferred and cast onto glass surface by pipetting. The nanofibril heterojunctions were fabricated by directly drop-casting the ethanol solution of the D molecules onto the nanofibers pre-deposited on the silica substrate. D-1 and D-2 were obtained as disclosed in Example 2; D-3 was directly obtained from Sigma-Aldrich. The concentrations of ethanol solution as employed for D-1, D-2, and D-3 were 0.1, 1, and 1 mM, respectively.

The A-2 nanofibers were fabricated in the same way.

The A-3 film was fabricated by drop-casting a chloroform solution of A-3 (20 nM) on the substrate.

Property Characterization of Nanofibers:

Fluorescence spectra of A-1 nanofibers and A-3 film were measured on a LS 55 fluorometer. The fluorescence spectra of A-2 fibers (with too low fluorescence quantum yield to be measured by ordinary fluorometer) were measured with a Leica DMI4000B inverted microscope (which provides excitation in the range of 530-560 nm) coupled with an Acton SP-2356 Imaging Spectrograph system and Acton PIXIS 400B Digital CCD Camera System for full spectra recording. SEM measurement was performed with a FEI NanoNova 6300 microscope, and the samples were directly drop-cast on a silica substrate. No metallic coating is needed for this field-emitting mode SEM, helping precisely reveal the morphology and size change of nanofibers upon coating of D materials. AFM measurement was performed in tapping mode on a Veeco MultiMode V scanning probe microscope.

Electrical Measurement with Nanofibers:

Electrical current measurements of the nanofibers were carried out using a two-probe method on a Signatone S-1160 Probe Station combined with an Agilent 4156C Precision Semiconductor Parameter Analyzer for high resolution current measurement. The probe station was equipped with a Motic Microscope for poisoning and a CCD camera for in situ imaging of the device. The whole measurement system is housed in a shielding dark box to eliminate the RF noise and/or scattering light for low current and/or light sensitive measurements. The micro-gap electrodes were fabricated by photolithography on a silicon wafer covered with a 300-nm thick $SiO_2$ dielectric layer. The gold electrode pair used here was 14 or 90 μm in width and 5 μm in gap, and fully covered with nanofibers via drop-casting. A tungsten lamp (Quartzline, 21V, 150 W) was used as the white light source for photocurrent generation, and the light is guided into the probe station through a glass optical fiber, followed by focusing on the sample through the objective lens. The light power reaching the sample surface was measured by a photon detector.

Example 4

Study of a Nanofibers and the Nanofibril Heterojunctions with D Molecules

Figure 1:
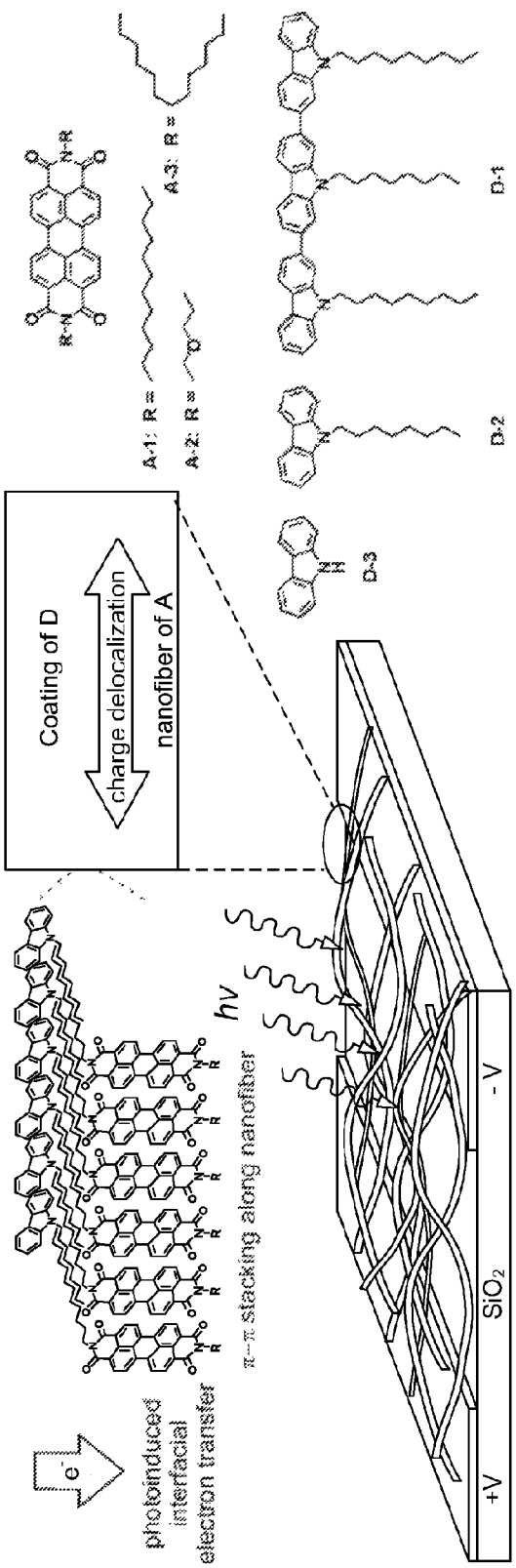
FIG. 1 is a schematic illustrating nanofibril heterojunctions composed of electron donor (D) coated nanofibers that function as electron acceptor (A) providing structures of A-1, A-2, A3, D-1, D-2, and D-3 in accordance with embodiments of the present invention.

Various nanofibers were studied and characterized. FIG. 1 provides for nanofibers from various combinations of an acceptor molecule (A-1, A-2, or A-3) with a donor molecule (D-1, D-2, or D-3). The π-π stacking along the long axis of nanofiber is conducive to the enhancement of charge transport due to the intermolecular π-electron delocalization. The photoinduced electron transfer in this case is more of an interfacial process, where the interdigitated alkyl chains can inhibit the back electron transfer to a certain extent depending on the length of the alkyl chains. Molecular structures of the three electron acceptors (A-1, A-2, A-3) and three electron donors (D-1, D-2, D-3) are shown in the right panel in FIG. 1.

Figure 2:
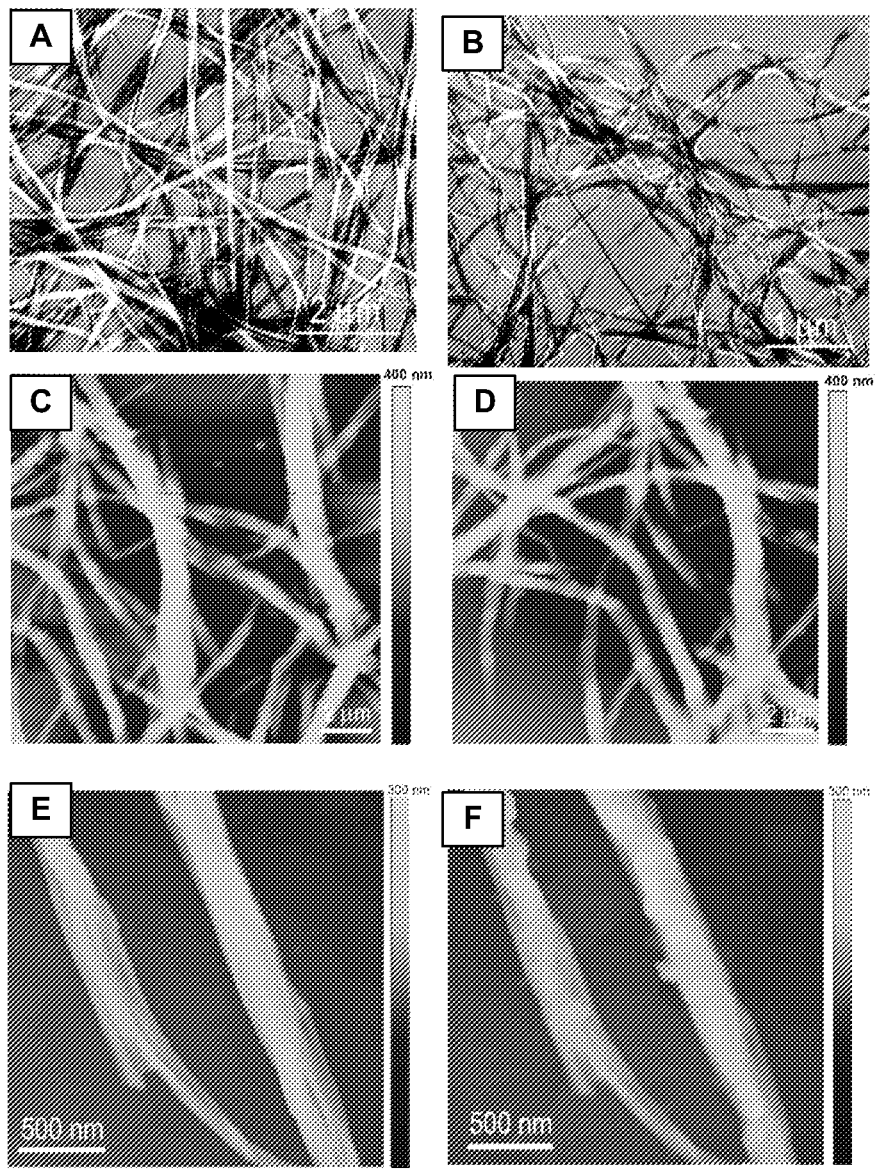
FIG. 2 provides SEM/AFM images of A-1 nanofibers of FIG. 1 before (a, c, e) and after (b, d, f) coated with D-1 of FIG. 1 a). SEM image of pristine nanofibers deposited on the silica. b). SEM image of the nanofibers (7.5 nmol A-1 molecules) after coated with D-1 by drop-casting an ethanol solution of D-1 (4 nmol) onto the fibril network as shown in 2a, where almost no separate phase of D-1 was formed in between the nanofibers. c) and e). AFM image of the same A-1 nanofibers as shown in 2a. d) and f). AFM image of the D-1 coated nanofibers as shown in 2b.

FIG. 2 shows nanofibers assembled from A-1 molecules. The nanofibers can be several microns long and tens of nanometers wide. Such thin nanofibers possess large surface area allowing for surface adsorption of donor (D) molecules to produce wide D/A interface, which in turn leads to efficient dissociation of excitons into separated charge carriers through interfacial electron transfer. Because the strong π-π stacking interaction between the A molecules (the perylene planes) results in effective π-electron delocalization, i.e., enhanced electron migration along the long axis of nanofiber, the separated charge carriers can be collected at two electrodes upon application of an electrical bias.

Figure 3:
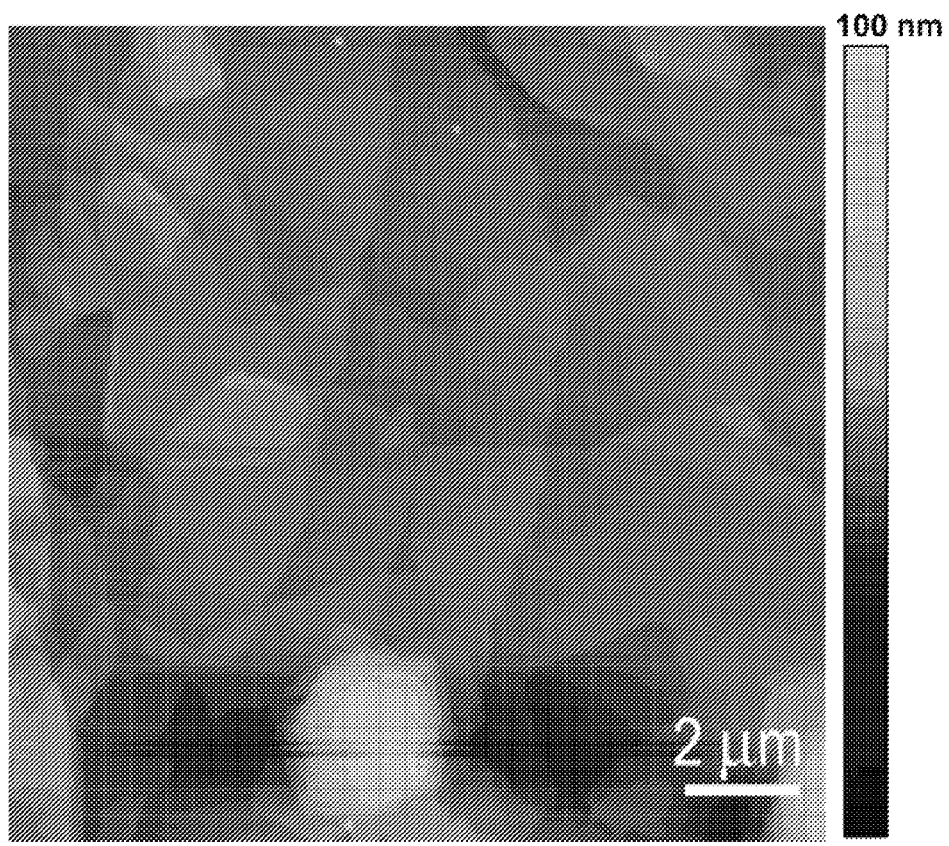
FIG. 3 is an AFM image of a D-1 film formed by drop-casting the ethanol solution (0.1 mM) onto a silica substrate.

With the nanofiber as an efficient charge conduit, the next critical criterion for achieving high photo current with the fibril heterojunctions is to inhibit the back electron transfer (i.e., charge recombination of the photogenerated electron and hole), which indeed represents one of the major causes of charge loss in bulk heterojunction materials, e.g., C60/polymers. To this end, the D-1 molecule (FIG. 1) was synthesized as discussed in Example 2, which possesses three long alkyl chains and is expected to strongly bind to the surface of the nanofibers that are self-assembled from the A molecules (e.g., A-1 of FIG. 1) with similar linear alkyl side-chains. The nanofibril heterojunctions were fabricated by simply drop-casting an ethanol solution of D-1 onto the A-1 nanofibers previously deposited on the silica substrate as discussed in Example 3. Notably, as evidenced by SEM and AFM images (FIG. 2b, 2d, 2f), most D-1 molecules were bound to the nanofibers upon vaporization of the solvent; between the nanofibrils, no apparent D-1 materials similar to the film morphology formed by direct drop-casting of the ethanol solution of D-1 onto the bare substrate (FIG. 3) were observed. Close examination of the AFM images clearly show the D-1 molecules were mostly adsorbed on the surface of the A-1 nanofibers (FIGS. 2e and 2f). Without intending to be bound by any particular theory, the spontaneous adsorption and concentration of D-1 molecules onto the A-1 nanofibers is likely driven by the hydrophobic interaction between the alkyl side-chains as mentioned above. By comparison, the highly hydrophilic surface of silica is not favored for strong binding with the D-1 molecules. Indeed, drop-casting the same D-1 solution onto silica led to the formation of broken films consisting of thin flakes and particulate aggregates, mainly caused by surface dewetting (FIG. 3). The observed one-step coating of D over A nanostructured materials provides a simple, clean method for constructing large area D/A heterojunctions with wide interfaces.

As such, nanofibril heterojunctions can minimize the formation of charge-transfer complexes of D-A because the A-1 nanofibers were pre-assembled without the interference of the D molecules and the fibril material is robust against the drop-casting solvent (i.e., A-1 molecules are insoluble in ethanol). In contrast, the formation of covalently linked D-A charge-transfer complexes is usually difficult to avoid in bulk heterojunction materials, where the intra-complex charge recombination dominates the loss of charge carriers. The nanofibril heterojunction system as presented in FIG. 1 also demonstrates practical advantages compared to the materials fabricated from covalently linked D-A molecules, which often require much more complicated molecular design and synthesis, and thus offer limited choices for the structural optimization of the D and A molecules.

As shown in FIG. 4a, high photoconductivity was observed for the nanofibril heterojunctions, whereas negligible photocurrent was measured for pristine A-1 nanofibers or the pure D-1 film (FIG. 5). The photocurrent also increased with the amount of D-1 added at the initial stage until a saturated region was reached at a molecular molar ratio of A-1 to D-1 of about 2. At this molar composition, the nanofibril heterojunction demonstrated a photocurrent on/off ratio above $10^4$ when measured on a micro-electrode pair (90 μm wide and 5 μm gap) under a bias of 10 V (FIG. 6). Given that the average irradiation light is 550 nm, the quantum efficiency of the photocurrent generation is estimated to be 8% under an electrical field of 2 V/μm by using the same calculation method previously reported (*Nano Lett.* 2004, 4, 1261-1265; *Adv. Mater.* 2006, 18, 2379-2383, which are incorporated herein by reference). The photocurrent was found to also switch promptly with light on and off (FIG. 4b), indicating a response time of only 200 ms. The fast photoresponse observed, together with the high on/off ratio, makes the nanofibril heterojunctions attractive for application in optoelectronic devices.

Consistent with the high photocurrent generation, the fluorescence of A-1 nanofibers was also effectively quenched upon adsorption of D-1 molecules (FIG. 4c). Without intending to be bound by any particular theory, since the absorption edge of D-1 is far below 400 nm, the observed fluorescence quenching of nanofibers is unlikely due to energy transfer, but rather solely to the interfacial electron transfer from D to the photoexcited A as illustrated in FIG. 1. Such photoinduced electron transfer is highly favorable with a driving force of 0.95 eV (FIG. 7). Notably, approximately 13% molar fraction of D-1 quenched approximately 55% of the fluorescence of A-1 nanofibers. Without intending to be bound by any particular theory, this amplified fluorescence quenching implies the existence of exciton diffusion within A-1 nanofibers, as previously indicated in other nanostructured systems. Since the nanofibril heterojunctions are formed by the adsorption of D-1 molecules via hydrophobic interaction between alkyl groups, it is expected that the adsorption and de-adsorption of D-1 can be readily switched, making the photoconductivity reversible. Indeed, the reversible photoconductivity was achieved simply by washing away the D-1 molecules with pure ethanol and re-deposition of the ethanol solution onto the nanofibers (FIG. 8). Considering the potential degeneration of the photoconductivity of organic materials caused by the photooxidation, the easy renewal of photoconductivity can be attractive for practical applications.

To gain an insight into the origin of the high photoconductivity shown in FIG. 4, we investigated various D and A molecules bearing different side groups (FIG. 1), which form the heterojunction interface and greatly affect the D/A interaction. As shown in FIG. 9, all the three D molecules demonstrated efficient fluorescence quenching of the A-1 nanofibers when coated onto the surface, indicating the occurrence of forward electron transfer from D to A upon photo-illumination. However, significant photocurrent was specifically obtained with D-1 and D-2 molecules bearing long alkyl groups, whereas D-3 generated negligible current under the same conditions. Without intending to be bound by any particular theory, the result implies that introduction of alkyl groups can effectively minimize the recombination of photogenerated charge carriers through spatial separation.

As such, the present disclosure provides for donor molecules and acceptor molecules having alkyl groups and companion alkyl groups having an affinity for each other that both enable the efficient forward electron transfer and effectively minimize the recombination of photogenerated charge carriers. Such an affinity can be achieved by atomic interactions including van der Waals interaction, hydrophilic interactions, hydrophobic interactions, or other atomic forces. In one example, the affinity can be achieved by hydrophobic interactions.

Compared to D-2, D-1 exhibited about six times higher photocurrent despite that fifteen times molar excess of D-2 was used. Without intending to be bound by any particular theory, this observation can be interpreted by the fact that the three alkyl chains borne with D-1 make its binding to the nanofibers much stronger, allowing for more efficient electron-transfer communication. The stronger interfacial binding is indeed supported by the higher fluorescence quenching efficiency observed for D-1 (FIG. 9). To further study the influence of side groups on the interfacial D/A interaction, nanofibers from A-2 molecules were fabricated as discussed in Example 3, which possesses the same π-scaffold as A-1, but bear short, more hydrophilic side-chains, which are not compatible with D-1 due to its hydrophobic side-chains. Indeed, the heterojunction system fabricated from A-2 nanofibers and D-1 molecules exhibited neither fluorescence quenching nor photocurrent generation (FIG. 9). This negative observation further supports the importance of alkyl groups to photocurrent generation.

To verify the critical effect of one-dimensional π-π stacking as featured by the nanofibril structure on photocurrent generation, another heterojunction was fabricated by adsorption of D molecules on a film of A-3. Due to the steric hindrance of the branched side groups of A-3, it is impossible to fabricate highly organized materials from this molecule, particularly with π-π stacking along one dimension. Although efficient electron transfer can take place at the D/A interface upon irradiation, as evidenced by significant fluorescence quenching of the film upon coating with D-3 and D-1 (FIG. 9), negligible photocurrent was observed for these film-based heterojunctions, likely owing to the lack of effective charge transport pathways within the film. This result, in turn, implies that the A-1 nanofibers as employed indeed play a critical role enabling rapid transport of the charge carriers towards the electrodes.

In conclusion, the present disclosure provides a nanofiber-based heterojunction approach to achieve high photoconductivity in organic semiconductor materials. Such nanofibril heterojunctions possess two prominent features that are critical for efficient photocurrent generation: the nanofibers both create large D/A interface for increased charge separation and act as long-range transport pathways for photogenerated charge carriers towards the electrodes, and the alkyl groups employed not only enable effective surface adsorption of D molecules on the nanofibers for effective electron-transfer communication, but also spatially separate the photogenerated charge carriers to minimize their recombination. The present disclosure provides a simple, adaptable method that allows for the development and optimization of photoconductive organic materials.

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth herein.

What is claimed is:

1. An organic nanofiber-based heterojunction material, comprising nanofibers of an acceptor molecule, the nanofibers coated with a donor molecule; wherein the acceptor molecule contains a group and the donor molecule contains a companion group;
wherein the group and companion group enables strong binding between the acceptor molecule and donor molecule, the strong binding providing for efficient collection of free charge carriers between the acceptor molecule and donor molecule, and wherein the group and companion group minimize charge carrier recombination between the acceptor molecule and the donor molecule.

2. The organic nanofiber-based heterojunction material of claim 1, wherein the donor molecule is a carbazole.

3. The organic nanofiber-based heterojunction material of claim 1, wherein the donor molecule is selected from the group consisting of

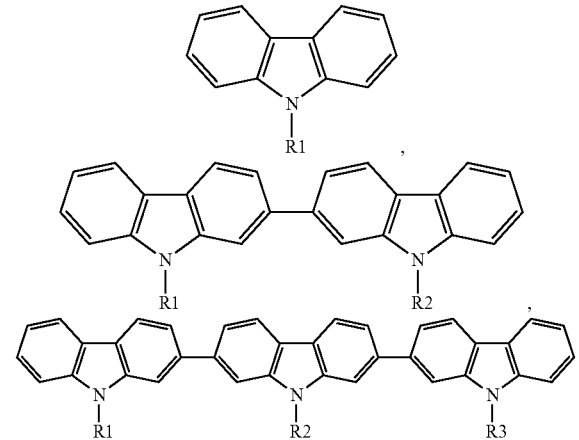

where R1, R2, and R3 individually represent the companion groups and are independently selected from the group consisting of H, branched alkyl, linear alkyl, substituted alkyl, unsubstituted alkyl, functionalized alkyls, and combinations thereof.

4. The organic nanofiber-based heterojunction material of claim 3, wherein the R1, R2, and R3 companion groups are independently selected from the group consisting of $C_2$-$C_{16}$ alkyls, $C_2$-$C_{16}$ alkyl ethers, $C_3$-$C_{20}$ branched alkyls.

5. The organic nanofiber-based heterojunction material of claim 3, wherein the R1, R2, and R3 companion groups are independently $C_2$-$C_{16}$ alkyls.

6. The organic nanofiber-based heterojunction material of claim 5, wherein the donor molecule is

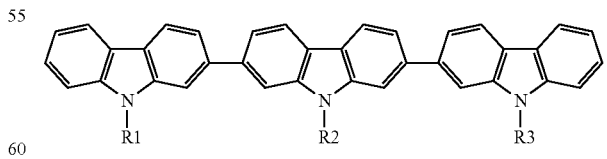

7. The organic nanofiber-based heterojunction material of claim 6, wherein at least one of the R1, R2, and R3 companion groups is different.

8. The organic nanofiber-based heterojunction material of claim 6, wherein the R1, R2, and R3 companion groups are the same.

9. The organic nanofiber-based heterojunction material of claim 1, wherein the acceptor molecule is

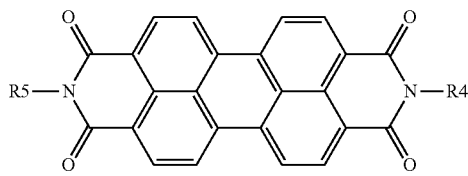

where R4 and R5 are the groups and are independently selected from the group consisting of H, branched alkyl, linear alkyl, substituted alkyl, unsubstituted alkyl, functionalized alkyl, and combinations thereof.

10. The organic nanofiber-based heterojunction material of claim 9, wherein the R4 and R5 groups are independently selected from the group consisting of $C_2$-$C_{16}$ alkyls, $C_2$-$C_{16}$ alkyl ethers, $C_3$-$C_{20}$ branched alkyls.

11. The organic nanofiber-based heterojunction material of claim 9, wherein the R4 and R5 groups are independently $C_2$-$C_{16}$ alkyls.

12. The organic nanofiber-based heterojunction material of claim 1, wherein the nanofibers are 1 μm to 10 μm in length and 10 nm to 100 nm in width.

13. The organic nanofiber-based heterojunction material of claim 1, wherein the efficient collection of free charge carriers is measured as a photocurrent generation quantum efficiency of the material of at least 8%.

14. The organic nanofiber-based heterojunction material of claim 1, wherein a photoresponse of the organic nanofiber-based heterojunction material is at the range of about 200 ms.

15. The organic nanofiber-based heterojunction material of claim 1, wherein organic nanofiber-based heterojunction material has a fluorescence quenching of 40-90%.

16. The organic nanofiber-based heterojunction material of claim 1, wherein the nanofibers have a wt % ratio of donor molecule to acceptor molecule of 1:20 to 20:1.

* * * * *